United States Patent [19]

Brooks et al.

[11] 4,253,851
[45] Mar. 3, 1981

[54] GAS PURIFICATION TREATMENT APPARATUSES, SYSTEMS AND PROCESS

[75] Inventors: Ray Brooks; Joe H. Lucero, both of Goodwell, Okla.

[73] Assignee: George A. DeMeritt, Texhoma, Okla.

[21] Appl. No.: 25,724

[22] Filed: Mar. 30, 1979

[51] Int. Cl.³ .............................................. B01D 47/02
[52] U.S. Cl. .......................................... 55/90; 55/95; 55/234; 55/256; 55/522; 55/523; 261/94; 261/DIG. 72
[58] Field of Search ............................ 210/150, 151; 261/94–98, 123, DIG. 72; 55/84, 90, 95, 234, 256, 314, 522, 523; 208/45

[56] References Cited

U.S. PATENT DOCUMENTS

| 468,408 | 2/1892 | June | 55/256 |
|---|---|---|---|
| 1,182,543 | 5/1916 | Ferguson | 55/90 |
| 1,939,924 | 12/1933 | Schimrigk | 261/DIG. 72 |
| 2,523,441 | 9/1950 | McKamy | 261/DIG. 72 |
| 2,817,689 | 12/1957 | White | 55/90 |
| 3,153,626 | 10/1964 | Kulik | 208/45 |
| 3,331,789 | 7/1967 | Clark | 208/45 |

FOREIGN PATENT DOCUMENTS

| 548737 | 3/1932 | Fed. Rep. of Germany | 55/523 |
|---|---|---|---|
| 955741 | 1/1957 | Fed. Rep. of Germany | 55/314 |
| 554358 | 6/1943 | United Kingdom | 55/314 |

*Primary Examiner*—Frank W. Lutter
*Assistant Examiner*—Gregory N. Clements
*Attorney, Agent, or Firm*—Ely Silverman

[57] ABSTRACT

Natural gas mixture containing suspended tarry particles and water as contaminants are purified by systems providing upward passage of such contaminated gas mixtures through interparticulate spaces in a vertically extending stable filter bed composed of hard lapilli-sized solid masses having internal vesicles connected to peripheral surfaces characterized by peripherally open glassy surfaced vesicles, said masses partially immersed in a volume of methyl alcohol.

5 Claims, 14 Drawing Figures

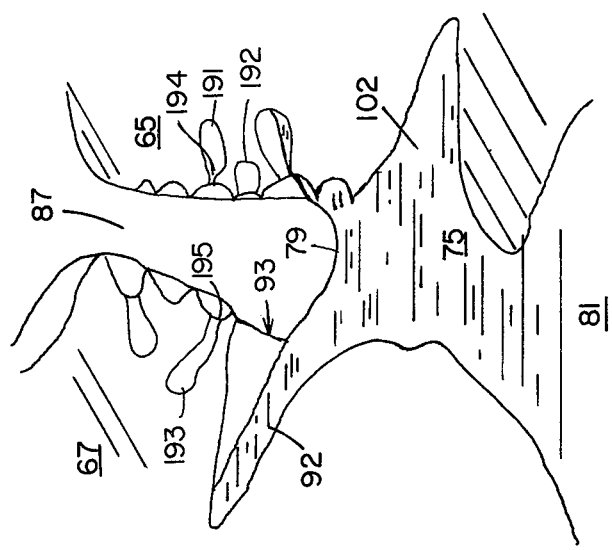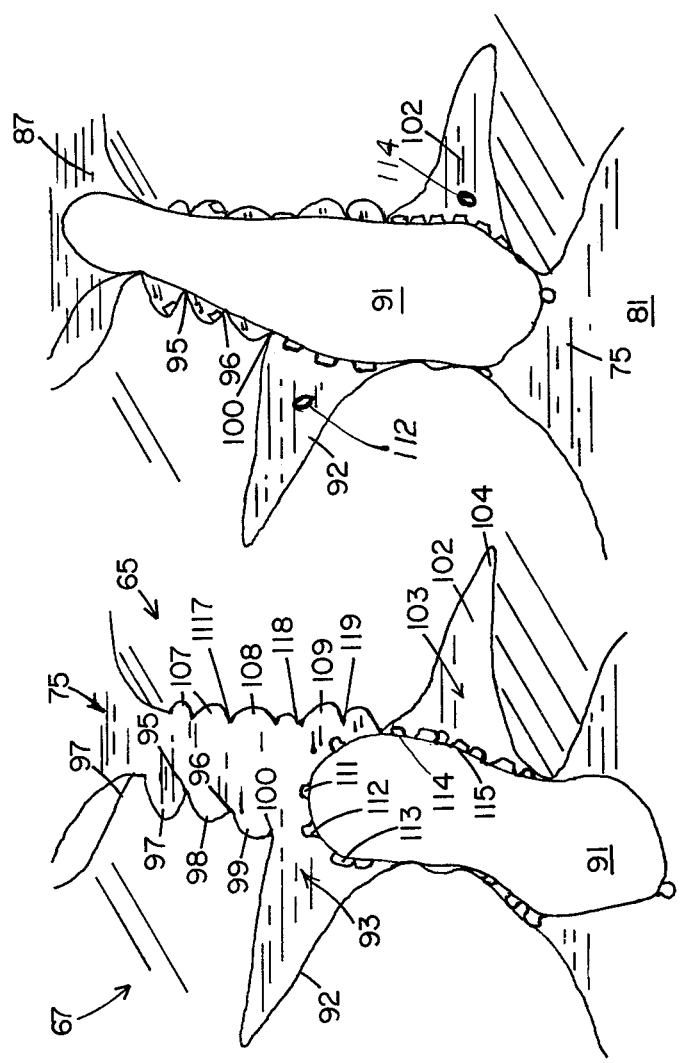

GAS PURIFICATION TREATMENT APPARATUSES, SYSTEMS AND PROCESS

BACKGROUND OF THE INVENTION

1. The Field of Invention

The field of art to which this invention pertains is gas purification.

2. Description of the Prior Art

The treatment of natural gas, which gas has, as impurities, additional to dust-like particulate grit, a small amount of water and, also, a small amount of tar-like and/or heavy oily material, has been a problem. While such water is present only in small amount, the condensation thereof is a difficult matter and the separation of even the condensed material is difficult. The separation of the small amounts of tar-like materials which are extremely finely divided is also a difficult problem and of such economic difficulty that it is frequently left untreated and, as a result, various appliances in which such gas is burned become corroded due to water and clogged by the accumulation of such tarry material in the orifices of such gas burning apparatuses. Plugging occurs because the small but definite amounts of oil and tar have melting points in excess of the usual temperatures of the orifices, notwithstanding the apparent proximity of such orifices to a flame, because such orifices are spaced definite distances from such flame and the cooling effect of the gas passing through the orifices to the flame prevents the vaporization of all such oily and/or tarry material, with a resulting accumulation of such material at the orifice and a plugging of such orifices with continued use. At or near Goodwell, Okla., for instance, plugging usually occurs after well within a year and the burners need to be periodically cleaned every few months. With the apparatus of this invention, over six months has passed without requiring any cleaning, and inspection of gas burners to which gas which had been treated by the apparatus of this invention has been fed shows them to be found free of accumulations of such oil and/or tarry deposits that are otherwise usual. Additionally, there has been no corrosion of gas orifices, notwithstanding that such corrosion is usual when the water content of the gas is not removed.

Conventional soft filter material as cloth and fiber filters change characteristics as they wear and, also, have such large holes that they do not provide for removal of the extremely finely divided particles when made sufficiently strong to withstand the pressures (usually 45 psig) and gas flows applied thereto.

SUMMARY OF THE INVENTION

A filter bed of solid particles formed of hard porous glassy material such as scoria, in cooperative combination with an initial volume of methanol in macropore spaces of such filter bed is used to treat a feed of natural gas, in which are suspended minute particles of heavy oils and/or tarry material as well as water, by the combination of steps of gas bubble formation, particle adsorption at bubble-gas-liquid interfaces in the bed macropore spaces, mechanical removal of adsorbed particles by the solid bed particles, dissolving of such removed particles in the liquid medium in the micropores or vesicles of the bed particles, and removal of the liquid medium and dissolved impurities.

The result of this operation is to remove water, which causes corrosion damage, and oil and/or tarry particles, which causes orifice plugging in gas-burning apparatuses. The methanol-liquid phase may then be centrifuged and/or distilled where the economics justify such treatment or, where only small amounts are involved and much handling would be required, a new batch of such relatively inexpensive methanol may be substituted for the used methanol liquid.

BRIEF DESCRIPTION OF THE DRAWINGS

FIG. 12 is a diagrammatic showing of an initial stage in the passage of a gas bubble and particles attached thereto through a zone of one macropore of FIGS. 2 and 11 in a stage of operation as shown in FIG. 3.

FIG. 13 diagrammatically shows, in the zone shown in FIG. 12, the operation of the filter medium solid particles on the bubble and the particles on its surface in a stage subsequent to the stage of operation shown in FIG. 12.

FIG. 14 is a diagrammatic view of the zone shown in FIGS. 12 and 13 during the step of draining liquid from bed 238.

Figure 4:
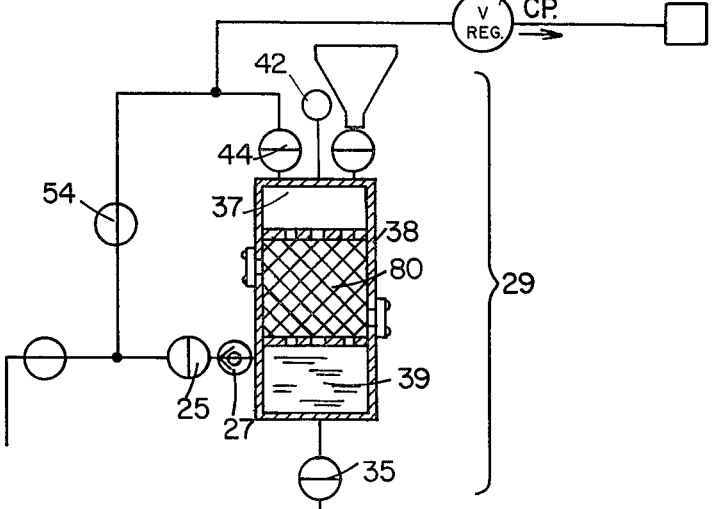
FIG. 4 is a diagrammatic showing of the apparatus of FIG. 1 in its stage of operation wherein the filtering operation is cut off but the gas flows to its point of use.
Figure 7:
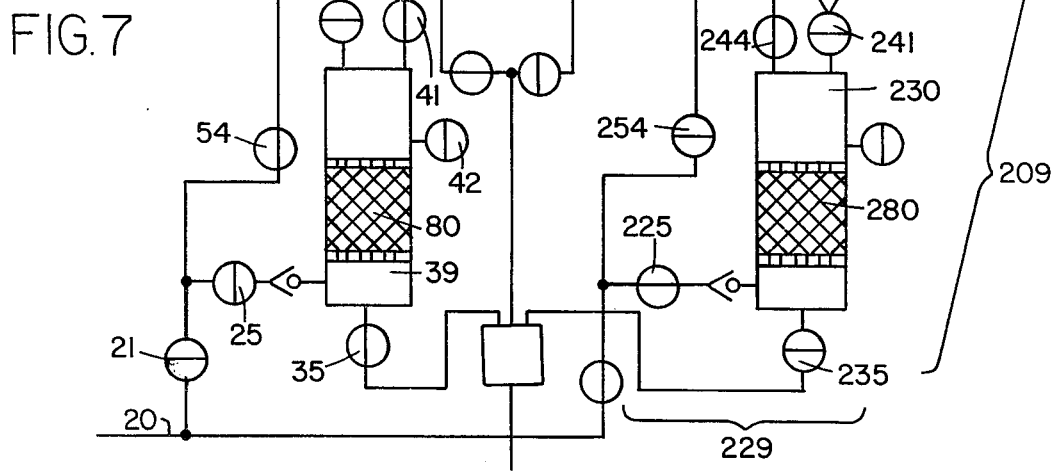
FIG. 7 diagrammatically shows the valve positions of appartus of FIG. 6 wherein one tank assembly 30 is cut-off and is being drained while second sub-assembly, 229, is being operated.

Diametral lines located within the circular diagrammatic valve outline and continuous with and parallel to lines connected to the valve outline indicate an open valve, as valves 21 and 54 in FIG. 4, while diametral lines located within the circular diagrammatic valve outline and transverse to and not continuous with lines connected to the valve outline indicate a closed valve, as shown for valves 25 and 44 in FIGS. 4 and 7.

Dimensions of a particular embodiment, 29, of apparatus according to this invention are set out at Table I.

The term methanol used herein means methyl alcohol and the term conduit covers the particular pipes referred to and illustrated as well as other gas-carrying tubes or lines.

DESCRIPTION OF THE PREFERRED EMBODIMENT

Figure 1:
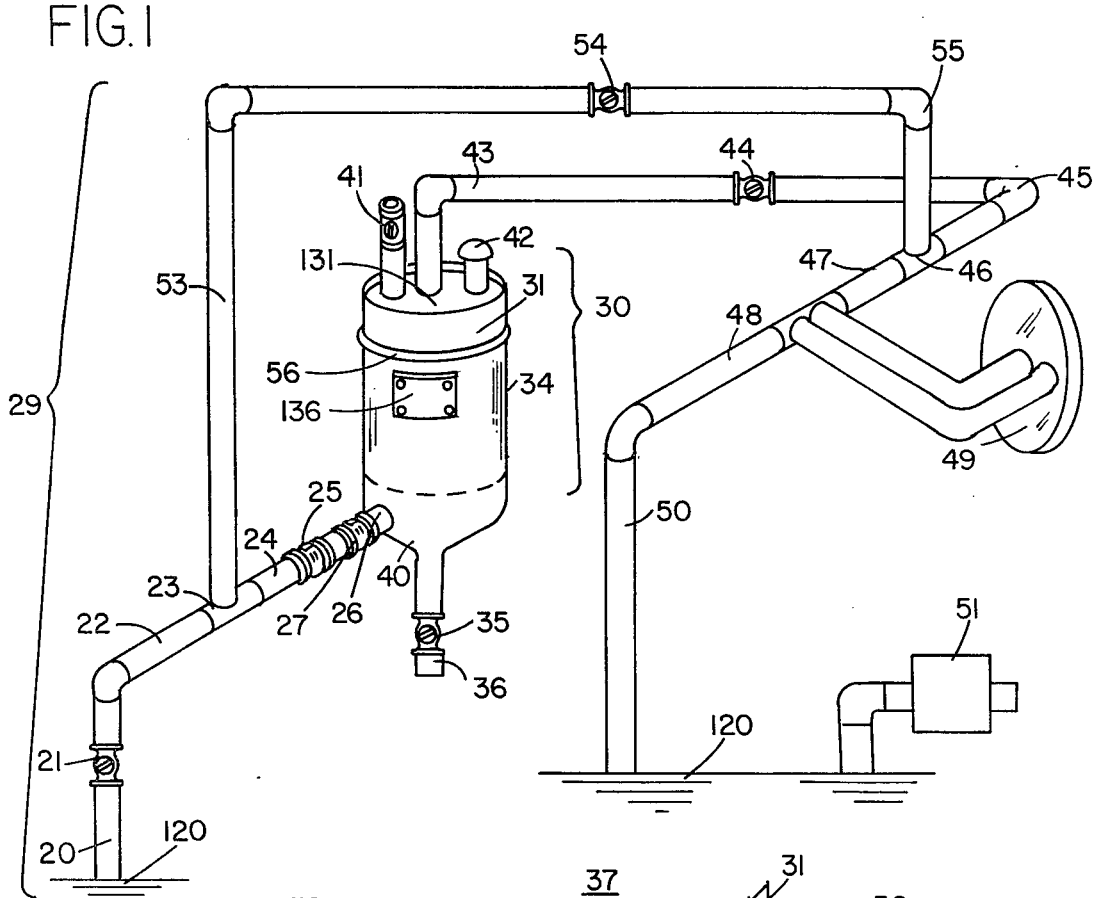
FIG. 1 is a perspective view of an apparatus according to this invention.

In one embodiment 29, of this invention schematically shown in FIG. 1, a gas inlet feed line 20 is a rigid pipe connected through a cut-off valve 21 to a rigid feed inlet pipe, line 22. A rigid wye 23 connects to a rigid inlet crossover pipe, line 53, and to a rigid tank inlet wye arm, 24. The arm 24 is a rigid pipe which is connected through a tank inlet line cut-off valve 25 to a rigid tank inlet pipe line 26 via check valve 27.

Figure 2:
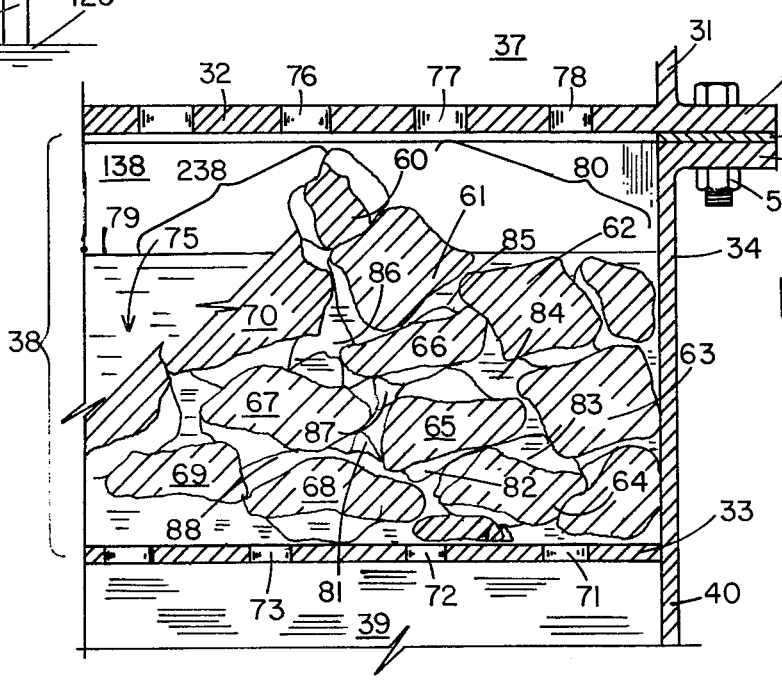
FIG. 2 is a diagrammatic overall showing of components in the gas treating bed chamber 38.

A rigid cylindrical filter bed tank 30 shown in FIG. 2 has a rigid top cap and plate 131 a rigid vertical cylindrical tank chamber side wall 34 and a rigid tank chamber tapered vertical bottom wall 40. Wall 40 connects the vertical side wall 34 to the top of chamber discharge bottom valve 35. The tank 30 is divided into a top gas collector chamber 37, a filter bed chamber 38 below the chamber 37 and a bottom gas feed chamber 39. Filter bed chamber 38 is below the top chamber 37 and separated therefrom by a top flat horizontal filter chamber perforated steel plate wall 32 firmly attached to side wall 34. The bottom chamber 39 and the filter chamber 38 are separated by a filter chamber bottom plate 33. The bottom plate 33 is a horizontal, flat perforated steel plate which is parallel to top wall 32 and is firmly attached to the side wall 34. The side wall 34 is an imperforate cylindrical vertically extending wall which is joined on its interior surface in gas-tight manner to the peripheral edges of both top chamber cap 31 and to bottom chamber wall 40.

A back flush valve 41 is connected through the top plate 131 and is firmly attached to plate 131 of top cap 31 for transfer of a liquid to the interior of filter chamber 38. A pressure relief valve 42 is located on top of the plate 131 and is firmly attached thereto. The valves 41 and 42 are horizontally separated from each other along the top of the plate 131.

A filter chamber outlet line 43 is a rigid pipe or conduit which operatively connects to the top chamber 37 of the tank 30. A cut-off valve 44 is connected to the filter chamber outlet line 43 and to an outer chamber outlet line 45; line 45 is a rigid ell (L-shaped pipe) that is connected to a tee arm line 46, and another branch of the tee 46 arm is tee branch line 47.

The base of the tee 46 is connected to the crossover outlet pipe, line 55. Valve 54 is a cut-off valve which is connected at one, outlet, side theretof to the crossover outlet line 55 and at its other, inlet, side to the crossover inlet line 53. A constant pressure discharge regulator 49 valve is connected at its inlet to line 47, and at its outlet to the pressure regulator discharge line 48. The discharge line 48 is a rigid pipe that feeds to the system assembly discharge line 50; line 50 is a rigid pipe and, with pipe 48, supports regulator 49. Line 50 passes to a gas burner apparatus 51.

A filter bed 238 is formed of a porous mass 80 and body of liquid 75 between plates 32 and 33 in chamber 38.

Figure 9:
FIG. 9 is a macrophotograph showing several exemplary solid components of bed 38, some of which components are shown in partial section, and showing a scale graduated in numbered inches (5, 6, 7, and 8) to illustrate the size, shape and texture and relations of such components in the filter bed chamber 38.
Figure 10:
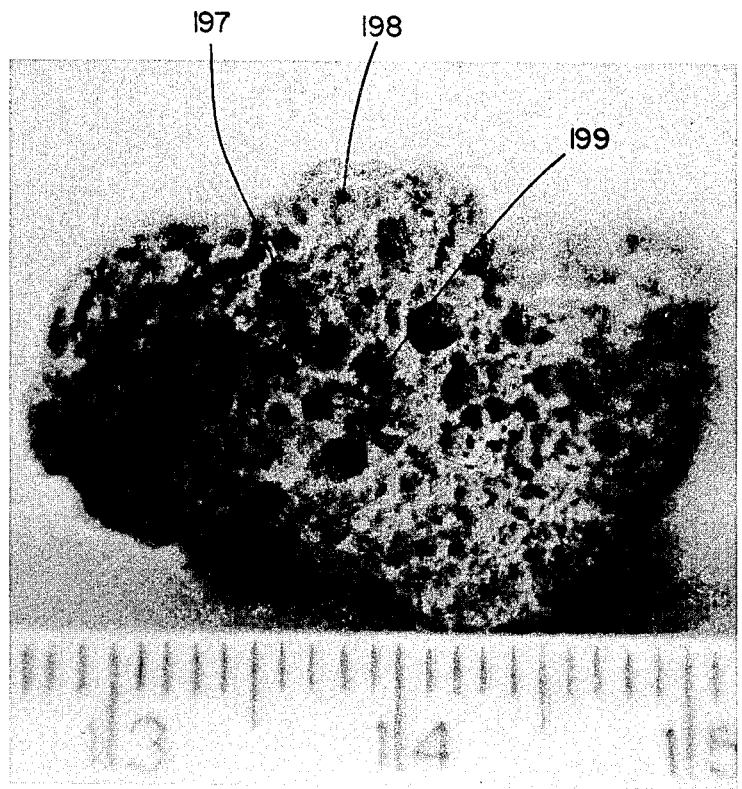
FIG. 10 is a sectional macrophotographic view of an exemplary solid bed component to show details of typical vesicle walls and surface, and with a centimeter scale (numbered 13, 14 and 15) with millimeter graduations between numbers.
Figure 11:
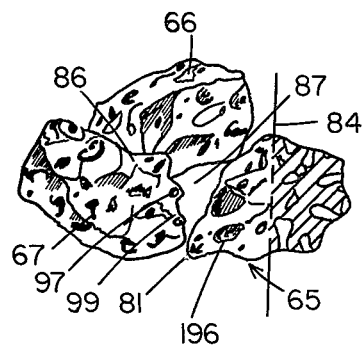
FIG. 11 is a diagrammatic showing of surface outlines and micropores of particles shown in FIG. 2 adjacent to an interparticle space or macropore 87.

Chamber 38 encloses space 138 within portion of tank 30 between plates 32 and 33, a porous mass 80 of discrete vesicular bed particles as 61–70, with macropores as 81–88 between the particles as 61–70, and a body of liquid 75. The chamber space 138, within tank 30 between plates 33 and 32, is filled to ¾ of its height with liquid 75 and to a greater height with bed particles as 61–70 which are light in weight, formed of tough material, provided with vesicles and micropores that have smooth surfaces and the walls of which particles have sharp peripheral edges as shown in FIGS. 9 and 10. The particles as 61–70 used in the bed 238 have particle sizes of ½ to 1¼ inch in overall length, are usually or generally ¼ to ¾ inch in thickness and from ¼ to ¾ inch in depth (measured transverse to the particle length and thickness); for the particular gas flow rates herein used the upper few inches of particles are not immersed in liquid 75 while the major portion of the mass of the particles as 61–70 is below upper surface 79 of liquid 75 at rest.

FIG. 2 diagrammatically shows a group of particles as 60–70 each having a structure generally as shown in FIG. 10 with each particle of such mass of particles (60–70) located in chamber 38 on top of the lower plate 33. The plate 33 is provided with a series of ⅛th inch diameter holes as 71–73 while the plate 32 has similar holes 76, 77, and 78. The liquid as 75 has an upper surface 79 below plate 32.

The solid filter bed components 61–70 are fragmental products of volcanic explosions known as pyroclastic rocks or fragments. On the basis of size they are called lappilli (as they are 1/6th to 1¼ inches in average diameter) and, as such loose fragments are formed of frothy material, they are known as scoria. Such sized scoria are fine grained glassy igneous rocks, the principal (50–75% by weight) component of which is silica, and, dependent upon the magma from which the glassy scoria is formed, such scoria also contain varied amounts (2–20%) by weight of $Al_2O_3$, $Fe_2O_3$, MgO, CaO, $Na_2O$, and/or $K_2O$. The solid component of the lapilli are essentially tough chill-tempered glasses, i.e., because the material is formed by rapid cooling and the inner portion cools more slowly than the surface, the interior continues to contract after the surface is essentially rigid, whereby compressive stresses develop in the surface layer with compensating tensile stresses in the interior: this results in a very tough as well as a hard glassy structure. Such scoria is essentially a porous variety of obsidian. As shown in FIGS. 9 and 10 the vesicles are rather large (up to 2 mm. diameter) so that the rock assumes a honeycomb appearance to the naked eye, as shown in FIG. 9. Some of the peripherally open vesicles are diagrammatically shown as 97, 98, and 79 in FIGS. 11–14. The surface hardness of the vesicles is 5.6 by Mohs' scale. While the texture is very fine grained to the naked eye, each of the vesicles have a glassy interior surface and have diameters down to 0.1 mm. Such materials are found in northern Arizona, Montana, Colorado, New Mexico, as well as in the northern and western United States. Typical vesicle shape, size and glassy wall texture are shown in FIGS. 9 and 10.

The scoria particles have a specific gravity of 1.35±0.05 and are wetted by methyl alcohol liquid 75 and sink in the alcohol liquid, which has a specific gravity of 0.79 at 20° centigrade and has a boiling point below 120° F. at 760 mm pressure.

At bottom of plate 32 the internal surface of tank wall 31 is firmly connected to plate 32. The external surface of wall 31 is firmly connected to a laterally extending flange 56. The top edge of the outer surface of wall 34 is firmly connected to a laterally extending flange 57. An annular gasket 58 is firmly held between flanges 56 and 57.

Flanges 56 and 57, and gasket 58 therebetween, as shown in FIG. 2, are removably yet firmly held together in liquid-tight and gas-tight fashion by nuts and bolts as 59 to allow for filling and emptying of solid contents of chamber 38. Plates 32 and 33 support and maintain mass 80 in location but their holes as 71–73 and 77–79 allow for passage of gas and liquid into and out of chamber 38; as shown in FIGS. 1, 3, 4 and 5, wall 34 of tank 30 may be provided with an upper inlet handhole 134 below plate 32 and with a lower outlet handhole 135 above plate 33 to load and reload solid filter bed constituents or masses as 60–70 to and from chamber 38. Each of the handholes 134 and 135 is provided with a closure plate 136 and 137, respectively, therefor, which plate is removably affixed to the tank wall 34 in a gas-tight and liquid-tight manner.

The macropore spaces as 81–88 located in the bed 238 between the bed particles as 61–70 are tortuous and irregular in horizontal cross-section, and in vertical longitudinal section, as shown in FIG. 2. Such macropores or interparticulate spaces occupy 50 ($\pm 2$)% of the interior volume of the porous mass 80. The average horizontal transverse diameter of the macropore spaces (measured transverse to the units of length of such passages between 4 to 6 contiguous bed particles adjacent to such increments of units of passages) is about ¼ inch (6 mm). As the bed particles have a small ($\pm 50$%) range of maximum length and like small ($\pm 50$%) range of maximum width and depth the total macropore volume or spaces in the total volume of the mass 80 produces bubbles as 91 of relatively ($\pm 50$%) uniform width and thickness (measured transverse to the length of such bubbles) from the gaseous feed mixture introduced into the feed chamber 39 at ambient temperature (40°–110° F.) at which the apparatus 29 operates.

In the particular embodiment shown, the specific gravity of the particles as 61–70 is 1.35 (i.e. density is 1.35 gm/cm$^3$), and the bulk density of mass 80 is 1.54 cm$^3$/gm. (754 gms. per 1160 cubic centimeters) so the interparticulate or macropore volume in mass 80 is 52% of the total mass volume while the micropore volume (or the average volume of the vesicles in each of the bed particles) is 48% of the particle volume, (on basis of specific gravity of solid obsidian is 2.6 gm./cm$^3$).

Macropores 81–88 are shown diagrammatically in FIGS. 2, 11, and 12–14; and an exemplary passage formed of series of such macropores is diagrammatically shown as extending from hole 72 in plate 32 via macropores 82, 81, 87, 86, 85 to upper liquid surface 79 in FIG. 2.

Figure 3:
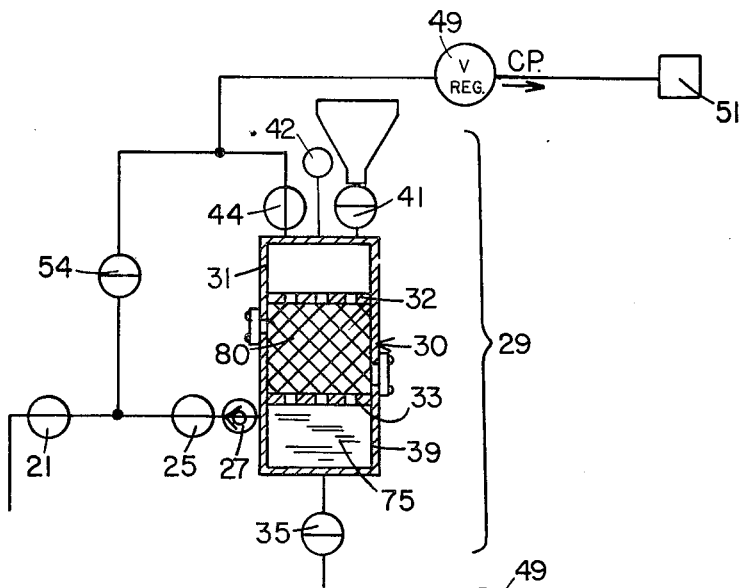
FIG. 3 is a diagrammatic presentation of valve positions during the gas treatment stage of operation of the apparatus of FIG. 1.

In normal operation, as shown in FIG. 3, valve 21 is in its open position and passes the to-be-treated gas and particle mixtures through the tank inlet line valve 25 to the lower chamber 39 of the tank 30. The filter chamber bottom valve 35 is closed and lower chamber 39 is, in major portion, filled with liquid 75. Mass 80 and liquid 75 and bubbles as 91 fill the major portion of chamber 38. The gas-particle mixture being treated by the material in chamber 38 enters by the line 26 into the chamber 39 and such volume of gas is dispersed first by the action of the plate portion of plate 33 and the holes as 71–73 therethrough. Such holes and plate provides for a passage of the gas-particle mixture into the porous mass 80 as bubbles and, thereafter, by interparticle macropores between the solid bed particles as 61–70 which provide for the further and/or continued breaking up of the gas feed into a series of small bubbles as 91 shown in FIGS. 12 and 13. Such bubbles pass through the macropore spaces as 81 between adjacent bed particles as 65 and 67. Each of the bed particles as 67 has some larger vesicles as 92 therein, each such vesicle having an average diameter at its peripheral opening 93 of about 2 mm and each such large vesicle or cavity extending into the mass 67 for about 4 to 6 mm. and as shown in FIG. 12 as diagrammatically representative of the larger size orifices that extend to the surface of each bed particle as 67. Similar orifices as 102 in other, adjacent, bed particles as 65 extend to the surface of such particles at a hole as 103 and extend interiorly to the vesicle base as 104.

The edges as 95 between vesicles 97 and 98 and like edges as 96 between vesicles as 98 and 99 and 100 between 99 and 92 are sharp-edged. Similar orifices as 107, 108 and 109 are found in the particles 65. Similar sharp intervesicular wall edges as 117 and 119 are also located between adjacent vesicles 107, 108 and 109 and adjacent orifice 102.

Each of the particles as 65 and 67 accordingly present hard sharp edges as 99 between adjacent vesicular orifices as 97 and 98 and like hard sharp edges as 100 between orifices 99 and 92. The surface hardness of such walls is about 6.5 on Mohs' scale. As particles as 110–115 of fine particles of tar which are adsorbed on the surface of bubbles as 91 pass upward through the liquid 75 in the macropore spaces as 81–88, those tar-like particles are engaged by the extremely sharp and tough edges as 95, 96, 100, 117, 118, 111, 119 of the bed particles as 61–70 and the bubbles as 91 are distorted in their upward passage through the tortuous passageways between the particles. These very fine and very sharp inter-vesicular wall edges, as shown in FIG. 10, engage the particles carried on the bubbles. The bubbles are forced against such edges; and tar particles, as 112, so forced into engagement with the wall edges, as shown in FIGS. 12 and 13, are scraped off the bubbles during the upward passage of the bubbles through the mass 80.

The vesicles 92, 97–99 of each of the bed particles as 61–70 form, together with vesicles as 191, 192, 193 on the interior of the particles, an open foam, i.e., the vesicles in the bed particles are in communication with each other through holes diagrammatically shown as 194, 195 and 196, and also shown in FIG. 10 as 197, 198 and 199. Because of the low surface tension of methyl alcohol (about 22 dynes/cm) and because the alcohol and gasses do not react with the bed particles and the alcohol readily wets or spreads on the glassy siliceous vesicle walls, the interior as well as exterior vesicles of all the bed particles below the level 79 of the liquid 75, as bed particles 61–70, are substantially full of alcohol when such particles are located in the alcohol-containing bed 80. The alcohol liquid increments located in the small vesicles are within static bed particles and are provided quiescent containment, and the tar-like particles as 112 freed from their being carried by and in the feed gas mixture as above described, once in such vesicles are mechanically protected from the turbulence of gasses passing rapidly through the macropores between the bed particles and the tar-like particles slowly but effectively dissolve in the methyl alcohol liquid in such vesicles. FIGS. 12 and 13 diagrammatically show two exemplary adjacent bed particles, 65 and 67 during movement of an exemplary bubble 91, also diagrammatically shown, passing upward through the mass of such bed particles.

Figure 5:
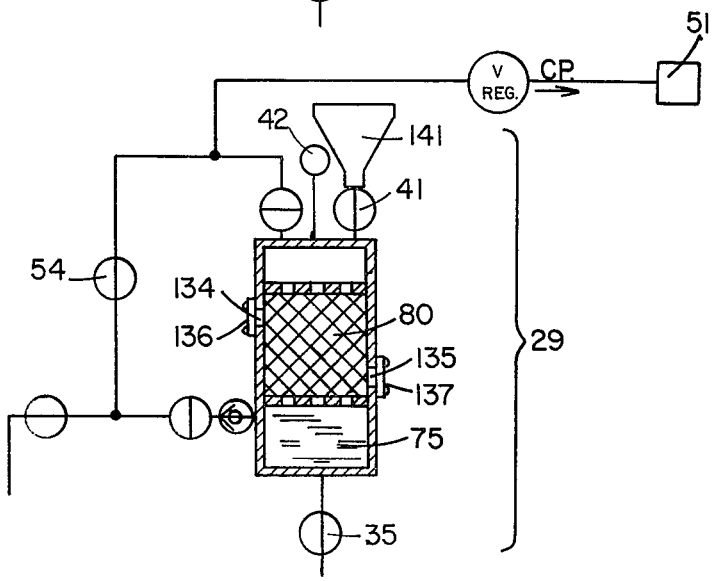
FIG. 5 diagrammatically shows the valve positions of the apparatus of FIGS. 1 and 3 during the stage of operation wherein the treatment of the feed has been stopped, gas flows uninterruptedly to apparatus 51 and the used treatment liquid is being removed and replaced.

When the valves 25, 35, 41, 44 and 54 are turned to their position shown in FIG. 5 the pressure in the chamber 38 is relieved and the liquid 75 and material dissolved therein is removed by passage downward through the open valve 35.

The smooth surface of the vesicles as 92, 97, 98, 102, 107, 108, and 109 of the bed particles as 65 and 67 of the mass 80 provide for a smooth movement of the liquid 75 out from such small cavities or vesicles located on the exterior surface of the bed particles and from the interiorly located vesicles which are effectively connected to such exteriorly located vesicles, as interior vesicle 193 connected by intervesicular hole 195 to vesicle 99, as well as all of the liquid in the macropore spaces of the chamber 38, during the flush operation illustrated in FIGS. 5 and 13. The liquid 75 is clear and colorless when initially added to the bed 38 but, after several months of use in the tank 30, when the liquid 75 is removed from the bed 38 (by opening valves 35 and 41 after closing valves 44 and 25) such liquid has a definite brown coloration and is cloudy.

The mechanical toughness of the bed particles which provides that they do not crumble and do not lose their smooth vesicle surfaces and their chemically inert chracter relative to the gas and liquid 75 are critical to this operation; the materials chosen for this use have such characteristics.

In operation as in FIGS. 2–4 and 6–8, the methanol liquid serves to absorb the water which is in the gas feed mixture as an impurity and the resulting water-methanol mixture is a liquid with surface activity that provides for sufficiently strong adsorption of oily and/or tar-like impurities carried in the feed gas to provide for an initial zone of concentration of such oily and/or tar-like material at the surfaces of contact of such methanol-water liquid and the gas and later ready removal therefrom. Accordingly, the operation of the methanol liquid on the to-be-treated gas provides an improvement in the capacity of the methanol liquid to treat such gas, especially in combination with the glassy porous obsidian-like glassy material of which the bed particles as 61–70 are formed.

The water dissolves in the methanol to form a homogeneous water-methanol-liquid phase and the resultant water-methanol-liquid phase has surface characteristics which provide for selective adsorption of the oil and/or tarry particulate material at the interface of (a) such methanol-water-liquid and (b) the bubbles of gas formed by passage of the to-be-treated and treated feed gas through the macropores of the scoria particles and the therein held methanol-water liquid. Such liquid 75 wets or spreads on the surface of the scoria particles so the sharp intervesicular edges but are not effectively dulled by surface tension action of such liquid in contact with the bed particles. The upward movement of gas bubbles in the macropore spaces between the bed scoria particles provides for agitation of the gas-suspended tarry particles and their removal from the interior of the gaseous bubbles as 91 to the surface of the methanol-water-liquid in contact with such bubbles. Thereafter, the action of the hard sharp edges of the bed scoria particles, as 61–70, which edges are located between adjacent vesicles in each such scoria, provide for mechanical removal of the small yet discrete oil-tar particles as 112 and 114 in FIG. 13 from the interface of the bubbles and the methanol-water-liquid. Such removal occurs because the tarry particles which are initially adsorbed on the bubble walls are forcefully (e.g. at 45 psig) urged against the sharp hard edges of the walls between adjacent glassy walled vesicles forming the stationary porous scoria bed masses, and are thereby held from further upward movement, hence are moved downwardly relatively to the upwardly moving bubbles until such particles lose their attachment to the bubble surface and fall into the liquid in an adjacent vesicle, as 92 or 102. The quiescently contained liquid in the vesicles of the scoria adjacent to such moving bubbles provides a dissolving action on such tar particles. The methanol-water liquid is later readily and substantially completely removed from the scoria bed and carries therewith the theretofore dissolved oil and/or tar-like particles initially suspended in the gas treated.

The bed 38 is a mechanically stable one which is not jiggled about by the movement of the to-be-treated gas through the macropores as 81–88 of such treatment bed. Additionally, some bed particles as 60 extend above the top surface 79 of the liquid 75 in the chamber 38 and serve to force downward the remaining bed particles and maintain those solid bed particles as 61–70 in stable spatial relationships with each other during passage of gas through bed 238 notwithstanding the upward thrust provided on adjacent bed members by the passage of the gas bubbles through the macropores of the bed 238. As the bed particles as 61–70 are sufficiently large, the movement of the gas through the macropores as 81–88 does not disturb the spatial relations of the bed particles and, accordingly, the bed particles do not rub against each other, hence do not wear against each other, hence do not abrade each other and wear out the sharp edges of the intervesicular walls at their peripheral edges (which edges engage the bubble surfaces as shown in FIGS. 12 and 13). At the same time, the bed particles are also sufficiently small that the tortuous yet continuous passages provided through the mass 80 for bubbles via the macropores between the bed particles diagrammatically shown as 61–70 are sufficiently small (average diameter of macropore space passage is $\frac{1}{4}$ to $\frac{1}{2}$ inch) to provide a large amount of gas-liquid interface between bubbles as 91 and liquid 75 for efficient adsorption of tarry material on such surfaces. The passages provide that the particles are sufficiently small that the macropore spaces between particles as 61–70 provide for adequately small sized bubbles.

The bed particles 61–70 are substantially all of similar size and shape, i.e., all $+\frac{3}{4}$ and $-1\frac{1}{2}$ inch long and $+\frac{1}{4}$, $-\frac{3}{4}$ inch in width and thickness and have rounded corners, so the macropore passages through mass 80 from top to bottom thereof are relatively uniform in size and shape and transverse cross-section for efficient tar adsorption and removal.

The center of the circular $\frac{1}{8}$ inch diameter holes as 71–73 and 77–79 in plates 32 and 33 are located along parallel straight lines spaced $\frac{1}{4}$ inch away from each other and the $\frac{1}{8}$ inch diameter holes are located with their centers $\frac{1}{4}$ inch apart along such straight lines so that the center of each of such holes are located at the corners of a square with edges $\frac{1}{4}$ inch long. Hence, the steel plates 32 and 33 each have a pore area of 18% of the total plate area. Such amount of passage area transverse to the $\frac{1}{8}$ inch thickness or height of those plates is less than the percentage of macropore or interparticulate space transverse cross-section relative to the transverse cross-section through the porous particle mass 80 as well as the hole size being less than the average transverse cross-section of the macropore passages. Accordingly, the porous plate 32 bears the force of the flow of upflowing gas in chamber 39 and causes the dispersion of such gas into bubble form prior to its passage thorugh the mass 80 and so permits the porous mass 80 to be static and the bubbles to expand in their passage through such mass 80. Because the upper plate 33 has a smaller transverse pore section than the porous mass 80, it maintains a pressure drop across said plate which protects the uppermost layer of bed particles from movement relative to the other portions of the bed during surges of gas flow through the filter bed chamber 38.

In summary, the structure and chemical relations of the filter bed 80 provide disruption of the to-be-treated gas into smaller bubbles and initial adsorption of tar particles on the surface of bubbles and engagement of such adsorbed tar particles by the free edges of the intervesicular walls of the bed particles as 61–70, and resultant holding or capture of finely divided tar-like particles. Such holding is a prerequisite for and provides, as above described, for a protracted time of liquid and tar particle contact within the bed particle vesicles as 92 and 102 and deeper vesicles as 191 which allows time for dissolving or dispersion of such tar-like material within the body of liquid 75 until it is discharged.

The masses of scoria as 61–70 and the tortuous macropore spaces therebetween which particles and macropore spaces extend above the surface of the static level 79 of the liquid 75 serve not only to (a) hold down the solid particles therebelow notwithstanding upward force of gas and bubbles on the mass of particles as 61–70 therebelow but also serve to (b) catch droplets of the liquid media carried by the rising gas stream passing through bed 238 which droplets result from the disruption of bubbles at the upper surface as 79 (when bed 80 is static) of the liquid 75 and also (c) provide a large wetted surface area on the liquid portion of which the oil or tar-like particles are adsorbed and from which surfaces such particles are therafter carried downward by the liquid layer on such wetted surfaces to the main mass of liquid 75 whereat such particles are dissolved and the resultant liquid suspension held until discharged as in FIGS. 5 and 7.

FIGS. 3–5 show stages in the operation of the apparatus 29.

FIG. 3 is a diagrammatic presentation of closed position of valves 35, 41, 42 and 54 during the gas treatment stage of operation of the apparatus of FIG. 1 as gas flows through valves 21, 25, 27, bed 238, and valve 44 as above described.

FIG. 4 is a diagrammatic showing of the apparatus of FIG. 1 in its stage of operation wherein the filtering operation is cut off by closure of valves 25 and 44: this stage is preparatory to the stage shown in FIG. 5, but the gas flows to its point of use, 51, via open valves 21 and 54.

FIG. 5 diagrammatically shows the valve position of the apparatus of FIGS. 1 and 3 during the stage of its operation wherein the treatment of the feed has been stopped by closure of valves 25 and 44 and gas is flowing via open valves 21 and 54 to apparatus 51 uninterruptedly and the used treatment liquid is being removed via open valve 35 and replaced by open valve 41 from source 141 with removal of the used liquor from the macropore spaces of the bed 38 as shown in FIG. 14.

In embodiment 209 the constituent parts of such assembly 29 of embodiment 209 are exactly as in assembly 29 of FIGS. 1–5 and the numbered components of assembly 229 are structually and functionally the same as the components of FIGS. 1–5 which are identified by referent numerals 200 units lower than the components of subassembly 229.

Figure 6:
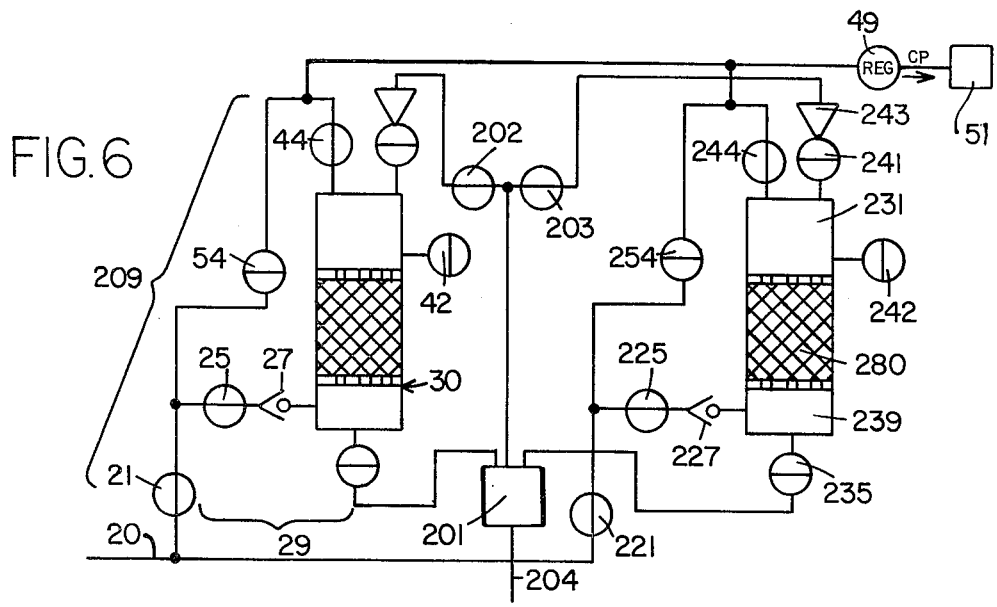
FIG. 6 is a diagrammatic showing of another embodiment of this invention using two subassemblies wherein the positions of the valve components of the system are shown in the stage of operation thereof wherein both subassemblies of the apparatus are operating.

FIG. 6 is a diagrammatic showing of embodiment 209, wherein the two like subassemblies 29 and 229, having the positions of their valve components 21, 25, 35, 41, 44 and 54, 221 and 225, 235, 241, 244 and 254 shown in the stage of operation wherein both like subassemblies 29 and 229 of the apparatus 209 are operating.

FIG. 7 diagrammatically shows the closed valve positions of valves 25 and 44 of apparatus of FIG. 6 wherein one tank assembly 30 is cut off and is being drained while the second subassembly, 229, is being operated via open valves 221, 225 and 244 while all other valves 235, 241, 242 and 254 are closed.

Figure 8:
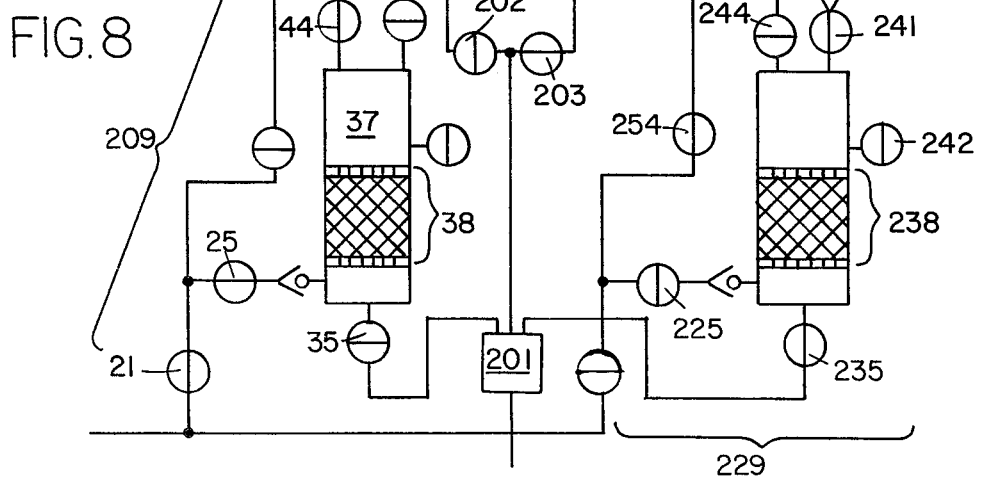
FIG. 8 shows the second tank subassembly, 230, of FIG. 6. being drained and flushed while the tank assembly 30 is operative to treat the gas passing to the point of use.

FIG. 8 shows the second tank assembly 230 of FIG. 6 being drained and flushed via open valves 235 and 241 while the tank assembly 30 is operative via open valves 25 and 44 to treat the gas passing to the point of use, 51.

A distilling apparatus 201 receives the used methanol-water liquid with dissolved and/or suspended tar particles therein and separates out and discharges the impurities at 204 and returns recovered liquor, via valve 202 to feeder 141, and by valve 203 to corresponding feeder 243 for tank 230.

The rigid pipes that form lines 21, 24, 53, and 54 provide a firm support for tank 30 at a height of bottom thereof above the ground 120 of about 2 feet which provides a convenient access by an operator to open valve 54 and close valves 44 and 25 and empty liquid contents of chamber 38 through valve 35, and to add additional liquid to chamber 38 via valve 41, as well as otherwise manipulate valves 25, 35, 41, 44 and 54.

The apparatus 29 treats from 2000 cubic feet per month to 10,00 cubic feet per month of natural gas containing water, tarry constituents, salt and sulfur, and effectively removes them all.

TABLE I

| DIMENSION OF THE PREFERRED EMBODIMENT | |
|---|---|
| Filter bed chamber 38 | |
| Tank 34, diameter | 8" |
| Plates 32–33, height | 24¾" |
| Plates 32–33, diameter | ⅞" |
| Pipes 20, 22, 53, 54 | |
| Diameter size | 1¼" |
| Pipe 48, Diameter size | 1¼" |
| Bed particle size, | |
| Average length, × width × thickness | 1" × ¾" × ¼" |
| Macropore volume, percent of mass 80 | 50% ± 5% |
| Micropore volume, percent of bed particles | 50% ± 5% |

We claim:
1. A gas treating apparatus comprising
(a) a gas feed inlet conduit,
(b) a vertically extending filter bed tank having a bottom end portion and a top end portion,
(c) a filter bed tank outlet conduit, and a filter bed outlet conduit cut-off valve,
(d) said gas feed inlet conduit connected to the bottom end portion of said vertically extending filter bed tank,
(e) said filter bed tank outlet conduit connected to the top end portion of said vertically extending filter bed tank in series with said filter bed outlet conduit cut-off valve, (f) a series-connected crossover conduit and crossover conduit cut-off valve connecting said gas feed inlet conduit and said filter bed outlet conduit at a conduit connection, said filter bed outlet conduit cut-off valve located between said conduit connection and said top end portion of said filter bed tank, said crossover conduit cut-off valve located between said conduit connection and said gas feed inlet conduit, (g) said vertically extending filter bed tank comprising a filter bed chamber, a filter bed in said chamber, said filter bed comprising:

(i) a mechanically stable porous mass of discrete glassy-surfaced porous particles, said mass of porous particles having an inter-particle macropore volume of substantially 50% of the volume of said mass of discrete porous particles, each of said discrete porous particles composed of a series of interconnected smooth-walled vesicles and having an intraparticulate vesicle volume of substantially 40% of each of said particle's volume, said interparticle macropores forming vertically extending passages in said porous mass which extend from the top to the bottom of said porous mass, (ii) a lower horizontally extending rigid perforate plate on the bottom of said bed and an upper horizontally extending rigid perforate plate above the top of said bed, each of said plates perforated by a plurality of equal sized orifices passing through said plate, and (iii) a volume of liquid in said filter bed chamber, said liquid extending to a vertical height in said filter bed chamber less than the maximum height of said porous mass and at least one-half of the height of said chamber as measured between said upper and lower horizontally extending rigid perforated plates, said porous mass of porous particles extending to a height greater than the height of said liquid in said filter bed chamber and to a height below the height of said upper perforated plate above said lower perforated plate in said filter bed chamber, said liquid wetting said glassy porous particles, said liquid being one in which water and tar are soluble and having a boiling point below 120° F. at 760 mm. pressure and wherein the ratio of (a) the area of the holes in said plates to the area of said plates is smaller than (b) the ratio of the transverse cross-section of the vertical passages in the porous mass to the transverse cross-section section of the porous mass and wherein the hardness of the vesicle walls of said particles is above 5.0 on Mohs' scale and wherein said liquid comprises methyl alcohol and the porous particles are formed of igneous rock.

2. Apparatus as in claim 1, wherein the top portion of said filter bed tank and the lower portions thereof are separable and are held together in gas-tight connection.

3. Apparatus as in claim 1, comprising also (a) a second gas feed inlet conduit,
(b) a second vertically extending filter bed tank having a bottom end portion and a top end portion,
(c) a second filter bed outlet conduit,
(d) a second gas feed inlet conduit connected to the bottom end portion of said second vertically extending filter bed tank,
(e) a second filter bed outlet conduit connected to the top end portion of said second vertically extending filter bed tank in series with a second filter bed outlet conduit cut-off valve to a second conduit connection,
(f) a second series-connected crossover conduit and cross-over conduit cut-off valve connecting said second gas feed inlet conduit to said second filter bed outlet conduit at said second conduit connection,
(g) a second vertically extending filter bed tank comprising a second filter bed chamber and a second filter bed in said second filter bed chamber, said second filter bed like said filter bed,
(h) a gas feed inlet pipe manifold connected by a first feed cut-off valve to said first gas feed inlet conduit and by a second feet cut-off valve to said second gas feed inlet conduit, and
(i) a filter bed outlet conduit manifold connected to said conduit connection and to said second conduit connection.

4. Process of treating a stream of hydrocarbon gas containing tarry particulate impurities and water comprising the steps of (a) dividing said gas into a plurality of small streams of bubbles and passing said bubbles upwardly through liquid methanol located in vertically extending interparticle spaces of a mechanically stable stationary mass of porous chemically inert sharp-edged bed particles having surfaces wetted by said methanol, while then elastically deforming said bubbles, said bed particles being substantially equi-sized scoria of igneous rock, and being a mechanically stable porous mass of discrete glassy-surfaced porous particles, said mass of porous particles having an interparticle macropore volume of substantially 50% of the volume of said mass of discrete porous particles, each of said discrete porous particles composed of a series of interconnected smooth-walled vesicles and having an interparticulate vesicle volume of substantially 40% of each of said particle's volume, said interparticle macropores forming vertically extending passages in said porous mass which extend from the top to the bottom of said porous mass and wherein the hardness of the vesicle walls of said particles is above 5.0 on Mohs' scale, (b) adsorbing said tarry particles at the gas-liquid interfaces of said bubbles and said liquid methanol on the walls of said bubbles,
(c) removing said adsorbed particles from said bubble walls by contacting said deformed walls of said upwardly moving bubbles and particles located in said bubble walls with said sharp-edged bed particles,
(d) passing said removed tarry particles into quiescent volumes of said liquid methanol held within and by said bed particles in communication with said interparticle spaces and interior walls of said bed particles mechanically protect said quiescent volumes from contact with said upwardly moving bubbles,
(e) dissolving said tarry particles in said quiescent volumes of liquid methanol, (f) terminating the upward passage of said bubbles through said interparticle spaces,
(g) draining off said liquid methanol and the dissolved material therein from said interparticle spaces and from the interior of said bed particles, and
(h) adding fresh liquid methanol to said interparticle spaces.

5. Process as in claim 4 wherein the said process of treating of a stream of hydrocarbon gas containing tarry impurities and water comprises also the step of concurrently operating a second series of steps duplicating the said steps (a) through (h) on a second stream of gas in parallel with said first series of steps (a) through (h), and where said steps (a) through (h) are operated alternately on each of said streams of gas and concurrently on both streams of said gas.

* * * * *